United States Patent [19]
Warnant et al.

[11] 3,974,182
[45] Aug. 10, 1976

[54] INTERMEDIATES FOR THE PREPARATION OF TRIENIC STEROIDS

[75] Inventors: Julien Warnant, Neuilly-sur-Seine; Jean Jolly, Fontenay-sous-Bois, both of France

[73] Assignee: Roussel-UCLAF, Paris, France

[22] Filed: June 25, 1975

[21] Appl. No.: 590,267

Related U.S. Application Data

[62] Division of Ser. No. 400,170, Sept. 24, 1973, Pat. No. 3,910,961, which is a division of Ser. No. 213,731, Dec. 29, 1971, Pat. No. 3,781,311.

[30] Foreign Application Priority Data

Mar. 19, 1971 France .............................. 71.09709

[52] U.S. Cl. .......................... 260/340.9; 260/586 E; 260/397.45
[51] Int. Cl.² ....................................... C07D 317/72
[58] Field of Search ................................ 260/340.9

*Primary Examiner*—Ethel G. Love
*Attorney, Agent, or Firm*—Hammond & Littell

[57] ABSTRACT

Novel intermediates for the preparation of trienic steroids which intermediates have the formula

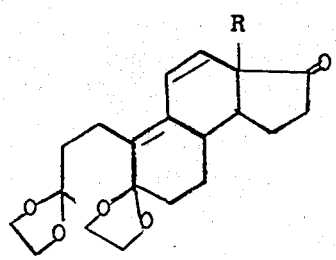

and

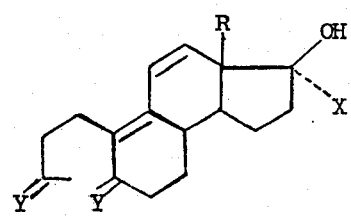

wherein R is alkyl of 1 to 4 carbon atoms and X is selected from the group consisting of aliphatic of 1 to 6 carbon atoms optionally substituted and cycloalkyl of 3 to 6 carbon atoms and Y is selected from the group consisting of =O and ethylenedioxy.

2 Claims, No Drawings

INTERMEDIATES FOR THE PREPARATION OF TRIENIC STEROIDS

PRIOR APPLICATION

This is a division of Ser. No. 400170 filed Sept. 24, 1973, now U.S. Pat. No. 3,910,961, which in turn is a division of copending, commonly assigned application Ser. No. 213,731 filed Dec. 29, 1971, now U.S. Pat. No. 3,781,311.

STATE OF THE ART

The compounds of formula I have interesting physiological properties, namely progestomimetic, androgenic or anticholesterolemic activity. French Pat. No. 1,492,782 describes the preparation of 13$\beta$-ethyl-17$\alpha$-ethynyl-$\Delta^{4,9,11}$-gonatriene-17$\beta$-ol-3-one (compound of formula I where R is —$CH_2$—$CH_3$ and X is —C ≡ CH) by reacting 13$\beta$-ethyl-$\Delta^{4,9,11}$-gonatriene-3,17-dione to form 3-ethylenedioxy-13$\beta$-ethyl-$\Delta^{4,9,11}$-gonatriene-17-one, reacting the latter with an ethynylation agent to obtain 3-ethylenedioxy-13$\beta$-ethyl-17$\alpha$-ethynyl-$\Delta^{4,9,11}$-gonatriene-17$\beta$-ol and subjecting the latter to hydrolysis to form 13$\beta$-ethyl-17$\alpha$-ethynyl-$\Delta^{4,9,11}$-gonatriene-17$\beta$-ol-3-one.

OBJECTS OF THE INVENTION

It is an object of the invention to provide novel intermediates for the preparation of trienic steroids of formula I starting from a 4,5-seco-$\Delta^{9,11}$-gonadiene.

This and other objects and advantages of the invention will become obvious from the following detailed description.

THE INVENTION

The novel process for the preparation of trienic steroids of the formula

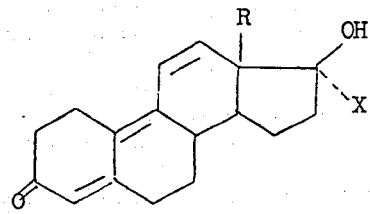

wherein R is alkyl of 1 to 4 carbon atoms and X is selected from the group consisting of aliphatic of 1 to 6 carbon atoms optionally substituted and cycloalkyl of 3 to 6 carbon atoms comprises reacting 13$\beta$-R-4,5-seco-$\Delta^{9,11}$-gonadiene-3,5,17-trione wherein R is alkyl of 1 to 4 carbon atoms with ethylene glycol in the presence of an acidic catalyst to selectively form 3,5-bis-ethylenedioxy-13$\beta$-R-4,5-seco-$\Delta^{9,11}$-gonadiene-17-one, reacting the latter with an organo-metallic compound wherein the organo is X as defined above to form 3,5-bis-ethylenedioxy-13$\beta$-R-17$\alpha$-X-4,5-seco-$\Delta^{9,11}$-gonadiene-17$\beta$-ol, subjecting the latter to acid hydrolysis to form 13$\beta$-R-17$\alpha$-X-4,5-seco-$\Delta^{9,11}$-gonadiene-17$\beta$-ol-3,5-dione and cyclizing the latter with a basic agent to form the corresponding 13$\beta$-R-17$\alpha$-X-$\Delta^{4,9,11}$-gonatriene-17$\beta$-ol-3-one.

In the compounds of formula I, R is preferably alkyl of 1 to 4 carbon atoms such as methyl, ethyl, propyl, isopropyl or butyl and X is preferably a saturated or unsaturated aliphatic radical optionally substituted such as methyl, ethyl, propyl, isopropyl, vinyl, allyl, 2'-methylallyl, isobutenyl, ethynyl, 1-propynyl, 2-propynyl, 2-butynyl, butadienyl, chloroethynyl or trifluoropropynyl or a cycloalkyl of 3 to 6 carbon atoms such as cyclopropyl, cyclopentyl or cyclohexyl.

The ketalization of the 3 and 5-keto groups with ethylene glycol is selective so that the 17-keto group is not ketalized. The acidic catalyst is preferably p-toluene sulfonic acid and the ketalization is preferably effected in the presence of a lower alkyl orthoformate such as ethyl orthoformate. This selective ketalization is remarkable because it is effected under mild conditions in excellent yields while the ketalization of the 3-keto group of $\Delta^{4,9,11}$-gonatriene-3,17-dione, a completely cyclized compound, as described in French Pat. No. 1,492,782 results in mediocre yields of 50 to 60%. The reaction is preferably effected at room temperature for a sufficient period for the keto in the 3- and 5-positions to both react.

The organo-metallic compound is preferably an organo-magnesium halide such as chloride, bromide or iodide or an organo alkali metal compound of the formula X—M wherein X is as defined above and M is an alkali metal such as lithium, sodium or potassium.

The acid hydrolysis may be effected with an inorganic acid such as hydrochloric acid or sulfuric acid or an organic acid such as acetic acid, citric acid or p-toluene sulfonic acid. The hydrolysis may be effected in one or more solvents such as alkanols such as methanol, ethanol or isopropanol, ketones such as acetone or a hydrocarbon such as benzene or toluene.

The basic agent for the cyclization is preferably a strong base. Examples are alkali metal alcoholates such as sodium methylate, sodium ethylate, sodium or potassium tert.butylate or potassium teramylate or an alkali metal hydroxide such as sodium hydroxide or potassium hydroxide.

Since each step and particularly the selective ketalization in the 3- and 5-positions is carried out with a very good yield, the process has the advantage over the already existing processes and particularly over the process of the French Pat. No. 1,492,782, to lead to a very high total yield of compounds of formula I, starting from a non-cyclized dienic derivative which is easily accessible in a steroid synthesis.

The 13$\beta$-R-4,5-seco-$\Delta^{9,11}$-gonadiene-3,5,17-triones used as starting materials can be prepared by dehydration of the corresponding 13$\beta$-R-4,5-seco-$\Delta^{9}$-gonene-11$\beta$-ol-3,5,17-trione with a dehydrating agent such as sulfuric acid.

In the following examples there are described several preferred embodiments to illustrate the invention. However, it should be understood that the invention is not intended to be limited to the specific embodiments.

EXAMPLE I

13$\beta$-ethyl-17$\alpha$-ethynyl-$\Delta^{4,9,11}$-gonatriene-17$\beta$-ol-3-one

STEP A:

3,5-bis-ethylenedioxy-13$\beta$-ethyl-4,5-seco-$\Delta^{9,11}$-gonadiene 17-one 5g of 13$\beta$-ethyl 4,5-seco-$\Delta^{9,11}$-gonadiene-3,5,17-trione were added to a mixture of 20 ml of ethylene glycol and 7.5 ml of ethyl orthoformate and then 0.10 g of p-toluene sulfonic acid was added thereto and the mixture was stirred at 20°C for 16 hours. 0.2 ml of pyridine was added to the mixture which was then cooled to 0°C and stirred for 1 hour at this temperature. The precipitate formed was recoverd by vacuum filtration, was washed and dried to obtain 6.05 g of 3,5-bis-ethylenedioxy-13β-ethyl-4,5-seco-Δ$^{9,11}$-gonadiene-17-one melting at 138°C and having a specific rotation $[\alpha]_D^{20} = -98.5°$ (c=0.5% in methanol containing 1% pyridine) which was used as is for the next step. A sample of the product was crystallized from methanol containing 1% pyridine for analysis.

Analysis: $C_{23}H_{32}O_5$; molecular weight = 368.49. Calculated: % C, 71.10; % H, 8.30; % O, 20.59. Found: %C, 71.0; % H, 8.4; % O, 20.8.

U V Spectrum (ethanol):

| | | |
|---|---|---|
| Inflex at 244 nm | $E_{1cm}^{1\%}$ | = 575 |
| max. at 249–250 nm | $E_{1cm}^{1\%}$ | = 604 |
| max at 289 nm | $E_{1cm}^{1\%}$ | = 16 |

The starting gonadiene was prepared as follows:

1 ml of ethyl ether was introduced at 0°C under an inert atmosphere into 2 ml of an aqueous solution of 66° Be sulfuric acid. Then, a suspension of 0.190 gm of 13β-ethyl-4,5-seco-Δ$^9$-gonene-11β-ol-3,5,17-trione was added thereto and the mixture was stirred for 15 minutes at +10°C. The reaction solution was then poured into a mixture of water and ice and extracted with methylene chloride. The methylene chloride extracts were combined, washed with water, with an aqueous sodium bicarbonate solution, again with water, dried and concentrated to dryness to obtain 13β-ethyl-4,5-seco-Δ$^{9,11}$-gonadiene-3,5,17-trione.

STEP B:
3,5-bis-ethylenedioxy-13β-ethyl-17α-ethynyl-4,5-seco-Δ$^{9,11}$-gonadiene-17β-ol 7.5 gm of potassium terbutylate were introduced into 50 ml of tetrahydrofuran and acetylene was bubbled therethrough for 30 minutes, 5 gm of 3,5-bis-ethylenedioxy-13β-ethyl-4,5,seco-Δ$^{9,11}$-gonadiene-17-one were added and the mixture was agitated for 1½ hours at 20°C with acetylene bubbling. The resulting suspension was poured into an aqueous solution of ammonium chloride and the mixture was agitated. The formed precipitate isolated by suction-filtration, and was washed and dried to obtain 5.23 gm of 3,5-bis-ethylenedioxy-13β-ethyl-17α-ethynyl-4,5-seco-Δ$^{9,11}$-gonadiene-17β-ol melting at 178°C which was used as is in the following step. A sample of this product recrystallized from methanol with 1% pyridine melted at 180°C and had a specific rotation $[\alpha]_D^{20} = -138°$(c =0.5% in methanol with 1% of pyridine)

Analysis: $C_{25}H_{34}O_5$; molecular weight = 414.52. Calculated: % C, 72.43; % H, 8.26. Found: % C, 72.2; % H, 8.2.

U V Spectrum (ethanol)

| | | |
|---|---|---|
| Infl. at 245 nm | $E_{1cm}^{1\%}$ | = 602 |
| max. at 249 nm | $E_{1cm}^{1\%}$ | = 617 |
| Infl. at 259 nm | $E_{1cm}^{1\%}$ | = 379 |

STEP C:
13β-ethyl-17α-ethynyl-4,5-seco-Δ$^{9,11}$-gonadiene-17β-ol-3,5-dione 5 gm of 3,5-bis-ethylenedioxy-13β-ethyl-17α-ethynyl-4,5-seco-Δ$^{9,11}$-gonadiene-17β-ol were introduced into 15 ml of acetone and after 7.5 ml of an aqueous solution of about 3N-hydrochloric acid were added, the mixture was agitated for 2 hours at 20°C. The resulting solution was poured into a water-ice mixture and agitated. The formed precipitate was isolated by vacuum filtration, was washed and dried to obtain 3.6 gm of 13β-ethyl-17α-ethynyl-4,5-seco-Δ$^{9,11}$-gonadiene-17β-ol 3,5-dione melting at 115°C which was used as is for the following step. A sample of this product recrystallized from ethyl ether melted at 116°C and had a specific rotation $[\alpha]_D^{20} = -85.5°$(c =0.5% in methanol)

Analysis: $C_{21}H_{26}O_3$; molecular weight = 326.42. Calculated: % C, 77.26; % H, 8.03. Found: % C, 77.3; % H, 7.7.

U V Spectrum (ethanol)

| | | |
|---|---|---|
| max. at 292 nm | $E_{1cm}^{1\%}$ | = 782 |

STEP D:
13β-ethyl-17α-ethynyl-4,9,11-gonatriene-17β-ol-3-one

In an inert atmosphere, 3 gm of 13β-ethyl-17α-ethynyl-4,5-seco-Δ$^{9,11}$-gonadiene 17β-ol-3,5-dione were dissolved in 15 ml of methanol, and then 5.4 ml of a 10% methanol solution of potassium hydroxide were slowly introduced. The resulting solution was refluxed for 2 hours and then cooled. 0.5 ml of acetic acid were added, and the reaction solution was poured in a water-ice mixture, cooled, and agitated. The formed precipitate was isolated by vacuum filtration, and was washed and dried to obtain 2.83 gm of crude product melting at 148°C.

The 2.83 gm of crude product were dissolved in methylene chloride and some Florisil (activated magnesium silicate) was added to the solution. The mixture was agitated and the Florisil was filtered off. The filtrate was concentrated to dryness by distillation under reduced pressure and the residue was added ethyl ether. The solution was refluxed, cooled, and agitated. The formed precipitate was isolated by vacuum filtration, and was washed and dried to obtain 2.6 gm of 13β-ethyl-17α-ethynyl-Δ$^{4,9,11}$-gonatriene-17β-ol-3-one melting at 150°C, and having a specific rotation $[\alpha]_D^{20} = +83°$(c = 1% in ethanol).

This compound is identical to that described in the French Pat. No. 1,492,782.

EXAMPLE II

Using the procedure of Example I, 4,5-seco-Δ$^{9,11}$-estradiene-3,5,17-trione was selectively reacted with ethylene glycol to obtain 3,5-bis-ethylenedioxy-4,5-seco-Δ$^{9,11}$-estradiene-17-one which was then reacted with potassium acetylide to form 3,5-bis-ethylenedioxy-17α-ethynyl-4,5-seco-Δ$^{9,11}$-estradiene-17β-ol.

The latter was then subjected to acid hydrolysis to form 17α-ethynyl-4,5-seco-Δ$^{9,11}$-estradiene-17β-ol-3,5-dione which was cyclized to form 17α-ethynyl-Δ$^{4,9,11}$-estratriene-17β-ol-3-one melting at 167°C and having a specific rotation $[\alpha]_D^{20} = +60°$(c = 0.5% in ethanol).

The product was identical to the compound described in French Pat. No. 1,453,214.

The starting estradiene is obtained from 4,5-seco Δ⁹-estrene 11β-ol 3,5,17-trione by a process analogous to the one described in step A of example I.

EXAMPLE III 3,5-bis-ethylenedioxy-4,5-seco-Δ⁹,¹¹-estradiene-17-one was reacted with methyl magnesium bromide to form 3,5-bis-ethylenedioxy-17α-methyl-4,5-seco-Δ⁹,¹¹-estradiene-17β-ol which was subjected to acid hydrolysis to form 17α-methyl-4,5-seco-Δ⁹,¹¹-estradiene-17β-ol-3,5-dione. The latter was cyclized to form 17α-methyl-Δ⁴,⁹,¹¹-estratriene-17β-ol-3-one melting at 169°C and having a specific rotation $[\alpha]_D^{20} = -57°$ (c = 0.5% in ethanol).

The product was identical to the compound described in French Pat. No. 1,426,077.

EXAMPLE IV 3,5-bis-ethylenedioxy-4,5-seco-Δ⁹,¹¹-estradiene-17-one was reacted with the lithium derivative of chloroacetylene to obtain 3,5-bis-ethylenedioxy-17α-chloroethynyl-4,5-seco-Δ⁹,¹¹-estradiene-17β-ol which was subjected to acid hydrolysis to form 17α-chloroethynyl-4,5-seco-Δ⁹,¹¹-estradiene-17β-ol-3,5-dione. The latter was cyclized to form 17α-chloroethynyl-Δ⁴,⁹,¹¹-estratriene-17β-ol-3-one melting at 193°C and having a specific rotation $[\alpha]_D^{20} = +128°$ (c = 0.6% in methanol).

The product was identical to the compound described in French Pat. No. 1,514,075.

EXAMPLE V

13β-n-propyl-4,5-seco-Δ⁹,¹¹-gonadiene-3,5,17-trione was selectively reacted with ethylene glycol to form 3,5-bis-ethylenedioxy-13β-n-propyl-4,5-seco-Δ⁹,¹¹-gonadiene-17-one which was reacted with potassium acetylide to form 3,5-bis-ethylenedioxy-13β-n-propyl-17α-ethynyl-4,5-seco-Δ⁹,¹¹-gonadiene-17β-ol. The latter was subjected to acid hydrolysis to form 13β-n-propyl-17α-ethynyl-4,5-seco-Δ⁹,¹¹-gonadiene-17β-ol-3,5-dione which was cyclized to form 13β-n-propyl-17α-ethynyl-Δ⁴,⁹,¹¹-gonatriene-17β-ol-3-one. The product after crystallization from ethanol and desolvation with hot water melted at 147°C and had a specific rotation $[\alpha]_D^{20} = +92°$ (c = 0.5% in ethanol).

The product was identical to the compound described in French Pat. No. 1,514,086.

EXAMPLE VI 3,5-bis-ethylenedioxy-4,5-seco-Δ⁹,¹¹-estradiene-17-one was reacted with cyclopropyl lithium to form 3,5-bis-ethylenedioxy-17α-cyclopropyl-4,5-seco-Δ⁹,¹¹-estradiene-17β-ol which was subjected to acid hydrolysis to form 17α-cyclopropyl-4,5-seco-Δ⁹,¹¹-estradiene-17β-ol-3,5-dione. The said product was cyclized to form 17α-cyclopropyl-Δ⁴,⁹,¹¹-estratriene-17β-ol-3-one.

| U V Spectrum | | |
|---|---|---|
| Max. at 344 nm | $E_{1cm}^{1\%}$ | = 825 |

The product is identical to the compound described in French Pat. No. 2,036,820.

Various modifications of the process may be made without departing from the spirit or scope thereof and it should be understood that the invention is to be limited only as defined in the appended claims.

We claim:
1. A compound of the formula

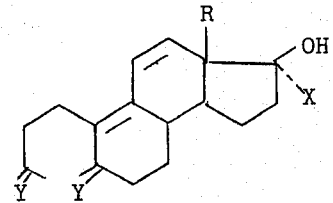

wherein R is alkyl of 1 to 4 carbon atoms, X is selected from the group consisting of aliphatic of 1 to 6 carbon atoms optionally substituted and cycloalkyl of 3 to 6 carbon atoms and Y is ethylenedioxy.

2. A compound of claim 1 which is 3,5-bis-ethylenedioxy-13β-ethyl-17α-ethynyl-4,5-seco-Δ⁹,¹¹-gonadiene-17β-ol.

* * * * *